United States Patent
Chon et al.

(10) Patent No.: US 9,549,851 B2
(45) Date of Patent: Jan. 24, 2017

(54) SURGICAL HAND PIECE WITH INTEGRATED PRESSURE SENSOR

(71) Applicant: Novartis AG, Basel (CH)

(72) Inventors: James Yong Chon, Irvine, CA (US); Robert Stephen Maurer, Jr., Huntington Beach, CA (US); Satish Yalamanchili, Irvine, CA (US)

(73) Assignee: Novartis AG, Basel (CH)

( * ) Notice: Subject to any disclaimer, the term of this patent is extended or adjusted under 35 U.S.C. 154(b) by 253 days.

(21) Appl. No.: 14/607,510

(22) Filed: Jan. 28, 2015

(65) Prior Publication Data

US 2016/0213515 A1 Jul. 28, 2016

(51) Int. Cl.
*A61B 17/32* (2006.01)
*A61F 9/007* (2006.01)
*A61B 17/00* (2006.01)
*A61M 1/00* (2006.01)

(52) U.S. Cl.
CPC ....... *A61F 9/00745* (2013.01); *A61F 9/00736* (2013.01); *A61M 1/0064* (2013.01); *A61B 2017/0046* (2013.01); *A61B 2217/007* (2013.01); *A61M 1/0025* (2014.02)

(58) Field of Classification Search
CPC ............ A61F 9/00745; A61F 9/00736; A61M 1/0064; A61M 1/0025; A61B 2017/0046; A61B 2217/007
See application file for complete search history.

(56) References Cited

U.S. PATENT DOCUMENTS

| | | | |
|---|---|---|---|
| 4,722,348 | A | 2/1988 | Ligtenberg et al. |
| 5,342,293 | A | 8/1994 | Zanger |
| 5,624,394 | A | 4/1997 | Barnitz et al. |
| 5,733,256 | A | 3/1998 | Costin |
| 5,795,328 | A | 8/1998 | Barnitz et al. |
| 5,810,765 | A | 9/1998 | Oda |
| 6,010,461 | A | 1/2000 | Haniff et al. |

(Continued)

FOREIGN PATENT DOCUMENTS

| | | |
|---|---|---|
| AU | 2011253755 A1 | 12/2011 |
| DE | 4131401 C1 | 11/1992 |

(Continued)

OTHER PUBLICATIONS

Mottaghi, M. et al., "Development of a Microsensor to Minimize Post Cataract Surgery Complications," World Academy of Science, Engineering and Technology 44, 2008, pp. 406-409.

(Continued)

*Primary Examiner* — Todd J Scherbel
*Assistant Examiner* — Son Dang
(74) *Attorney, Agent, or Firm* — Kenneth D. Bassinger

(57) ABSTRACT

A surgical hand piece comprises a shell, a channel having an irrigation conduit, and a sensor housing. The channel is coupled to the shell such that the proximal end of the channel is located at the proximal end of the shell and the distal end of the channel is located near the distal end of the shell. The sensor housing has an irrigation path extending through it. The sensor housing has a seal interface on one end. The seal interface end of the sensor housing is coupled to the proximal end of the channel such that the irrigation conduit of the channel is fluidly coupled to the irrigation path of the sensor housing.

20 Claims, 6 Drawing Sheets

(56) References Cited

U.S. PATENT DOCUMENTS

| | | |
|---|---|---|
| 6,193,656 B1 | 2/2001 | Jeffries et al. |
| 6,241,700 B1 * | 6/2001 | Leukanech ......... A61F 9/00745 604/19 |
| 6,425,883 B1 | 7/2002 | Urich et al. |
| 6,536,286 B1 | 3/2003 | Moyer et al. |
| 6,579,255 B2 | 6/2003 | Kadziauskas et al. |
| 6,712,764 B2 | 3/2004 | Jeffries et al. |
| 6,740,058 B2 | 5/2004 | Lal et al. |
| 6,780,166 B2 | 8/2004 | Kanda et al. |
| 6,896,664 B2 | 5/2005 | Novak |
| 6,997,896 B2 | 2/2006 | Novak |
| 7,083,601 B1 | 8/2006 | Cosmescu |
| 7,845,235 B2 | 12/2010 | Sandu et al. |
| 7,947,009 B2 | 5/2011 | Kubler et al. |
| 7,998,156 B2 | 8/2011 | Staggs |
| 8,162,919 B2 | 4/2012 | Cull et al. |
| 8,264,363 B2 | 9/2012 | Del Castilio et al. |
| 8,409,170 B2 | 4/2013 | Locke et al. |
| 8,439,874 B2 | 5/2013 | Hertweck |
| 8,622,923 B2 | 1/2014 | Pons et al. |
| 2008/0114290 A1 | 5/2008 | King et al. |
| 2009/0049522 A1 | 2/2009 | Claus et al. |
| 2009/0118663 A1 | 5/2009 | Rockley et al. |
| 2009/0306581 A1 | 12/2009 | Claus |
| 2011/0087156 A1 | 4/2011 | Claus et al. |
| 2011/0190690 A1 | 8/2011 | Humayun et al. |
| 2012/0065553 A1 | 3/2012 | Lebet |
| 2012/0215160 A1 | 8/2012 | Valenti et al. |
| 2012/0232466 A1 | 9/2012 | Kuebler et al. |
| 2013/0150782 A1 | 6/2013 | Sorensen et al. |
| 2014/0142493 A1 | 5/2014 | Claus et al. |

FOREIGN PATENT DOCUMENTS

| | | |
|---|---|---|
| DE | 102009049430 A1 | 6/2011 |
| EP | 0988826 B1 | 1/2002 |
| EP | 2004114 B1 | 10/2011 |
| EP | 1537840 B1 | 12/2011 |
| EP | 2320842 B1 | 6/2012 |
| EP | 2234660 B1 | 6/2013 |
| EP | 2488134 B1 | 8/2013 |
| EP | 1861052 B1 | 7/2014 |
| EP | 2227196 B1 | 9/2014 |
| JP | 5575906 B2 | 8/2014 |
| WO | 9315777 A2 | 8/1993 |
| WO | 2008157674 A1 | 12/2008 |
| WO | 2009150683 A2 | 12/2009 |
| WO | 2010014937 A1 | 2/2010 |
| WO | 2010014942 A1 | 2/2010 |
| WO | 2010086741 A1 | 8/2010 |
| WO | 2012041288 A2 | 4/2012 |
| WO | 2014195927 A1 | 12/2014 |

OTHER PUBLICATIONS

International Searching Authority, International Search Report and Written Opinion, PCT/US2015/063479, mailed Mar. 9, 2016, 11 pages.

\* cited by examiner

SURGICAL HAND PIECE WITH INTEGRATED PRESSURE SENSOR

BACKGROUND OF THE INVENTION

This invention relates generally to the field of ophthalmic surgery and more particularly to ultrasonic hand pieces for phacoemulsification.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial lens (IOL).

In the United States, the majority of cataractous lenses are removed by a surgical technique called phacoemulsification. During this procedure, a thin phacoemulsification cutting needle is inserted into the diseased lens and vibrated ultrasonically. The vibrating cutting needle liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven hand piece, an attached cutting needle, an irrigating sleeve, and an electronic control console. The hand piece assembly is attached to the control console by an electric cable and flexible tubing. Through the electric cable, the console varies the power level transmitted by the hand piece to the attached cutting needle and the flexible tubing supply irrigation fluid to and draw aspiration fluid from the eye through the hand piece assembly.

The operative part of the hand piece is a centrally located, hollow resonating bar or horn directly attached to a set of piezoelectric crystals. The crystals supply the required ultrasonic vibration needed to drive both the horn and the attached cutting needle during phacoemulsification and are controlled by the console. The crystal/horn assembly is suspended within the hollow body or shell of the hand piece by flexible mountings. The hand piece body terminates in a reduced diameter portion or nosecone at the body's distal end. The nosecone is externally threaded to accept the irrigation sleeve. Likewise, the horn bore is internally threaded at its distal end to receive the external threads of the cutting needle. The irrigation sleeve also has an internally threaded bore that is screwed onto the external threads of the nosecone. The cutting needle is adjusted so that the needle projects only a predetermined amount past the open end of the irrigating sleeve.

In use, the ends of the cutting needle and irrigating sleeve are inserted into a small incision of predetermined width in the cornea or sclera. The cutting needle is ultrasonically vibrated along its longitudinal axis within the irrigating sleeve by the crystal-driven ultrasonic horn, thereby emulsifying the selected tissue in situ. The hollow bore of the cutting needle communicates with the bore in the horn that in turn communicates with the aspiration line from the hand piece to the console. A reduced pressure or vacuum source in the console draws or aspirates the emulsified tissue from the eye through the open end of the cutting needle, the cutting needle and horn bores and the aspiration line and into a collection device. The aspiration of emulsified tissue is aided by a saline solution or irrigating solution that is injected into the surgical site through the small annular gap between the inside surface of the irrigating sleeve and the cutting needle.

During surgery, the console controls irrigation and/or aspiration which in turn determines the pressure in the eye. Aspirating too much fluid from the eye can result in low pressure and a shallowing or collapse of the anterior chamber. Typically, the pressure in the eye is monitored by measuring the pressure in the irrigation and/or aspiration lines. One or more noninvasive pressure sensors are located in a fluidics cassette to which the irrigation and/or aspiration lines are connected. The location of these pressure sensors, in a cassette that is remotely located from the eye, leads to some delay in monitoring pressure in the eye. It would be desirable to locate a pressure sensor close to the eye to minimize the delay in monitoring eye pressure.

SUMMARY OF THE INVENTION

In one example of the present invention, a surgical hand piece comprises a shell, a channel, and a sensor housing. The channel has proximal and distal ends. The channel is coupled to the shell such that the proximal end of the channel is located at the proximal end of the shell and the distal end of the channel is located near the distal end of the shell. The channel has an irrigation conduit passing through it. A sensor housing has an irrigation path extending through it and a seal interface on one end of the sensor housing. The seal interface end of the sensor housing is coupled to the proximal end of the channel such that the irrigation conduit of the channel is fluidly coupled to the irrigation path of the sensor housing. The sensor housing further comprises a cavity for receiving a pressure sensor. A pressure sensor assembly is located in the cavity and fluidly seals the cavity. The pressure sensor measures fluid pressure in the irrigation path of the sensor housing. The pressure sensor assembly further comprises: a flex circuit; circuitry coupled to the flex circuit; and wire terminations coupled to the flex circuit. The pressure sensor is coupled to the flex circuit. A plug bolt weldment is coupled to the sensor housing and the proximal end of the shell. The plug bolt weldment has a hollow interior. The pressure sensor assembly is at least partially located in the hollow interior of the plug bolt weldment. The sensor housing may also comprise an irrigation connector. A seal is located at the seal interface of the sensor housing.

In another example of the present invention, a surgical hand piece comprises a shell, a channel, and a sensor housing. The channel has proximal and distal ends. The channel is coupled to the shell such that the proximal end of the channel is located at the proximal end of the shell and the distal end of the channel is located near the distal end of the shell. The channel has an irrigation conduit passing through it. A sensor housing has an irrigation path extending through it and a seal interface on one end of the sensor housing. The seal interface end of the sensor housing is coupled to the proximal end of the channel such that the irrigation conduit of the channel is fluidly coupled to the irrigation path of the sensor housing. A pressure sensor assembly comprises a flex circuit and a pressure sensor coupled to the flex circuit. The pressure sensor is located in the cavity of the sensor housing and measures fluid pressure in the irrigation path. The pressure sensor fluidly seals the cavity. The pressure sensor assembly further comprises: circuitry coupled to the flex circuit; and wire terminations coupled to the flex circuit. A plug bolt weldment with a hollow interior is coupled to the sensor housing and the proximal end of the shell. The pressure sensor assembly is at least partially located in the hollow interior of the plug bolt weldment. The sensor housing further comprises an irrigation connector. A seal is located at the seal interface of the sensor housing. An end cap is coupled to the plug bolt weldment and seals the hollow interior of the plug bolt weldment. A nose cone is located at the distal end of the shell and the channel terminates at the nose cone.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION

Reference is now made in detail to the exemplary embodiments of the invention, examples of which are illustrated in the accompanying drawings. Wherever possible, the same reference numbers are used throughout the drawings to refer to the same or like parts.

Figure 1:
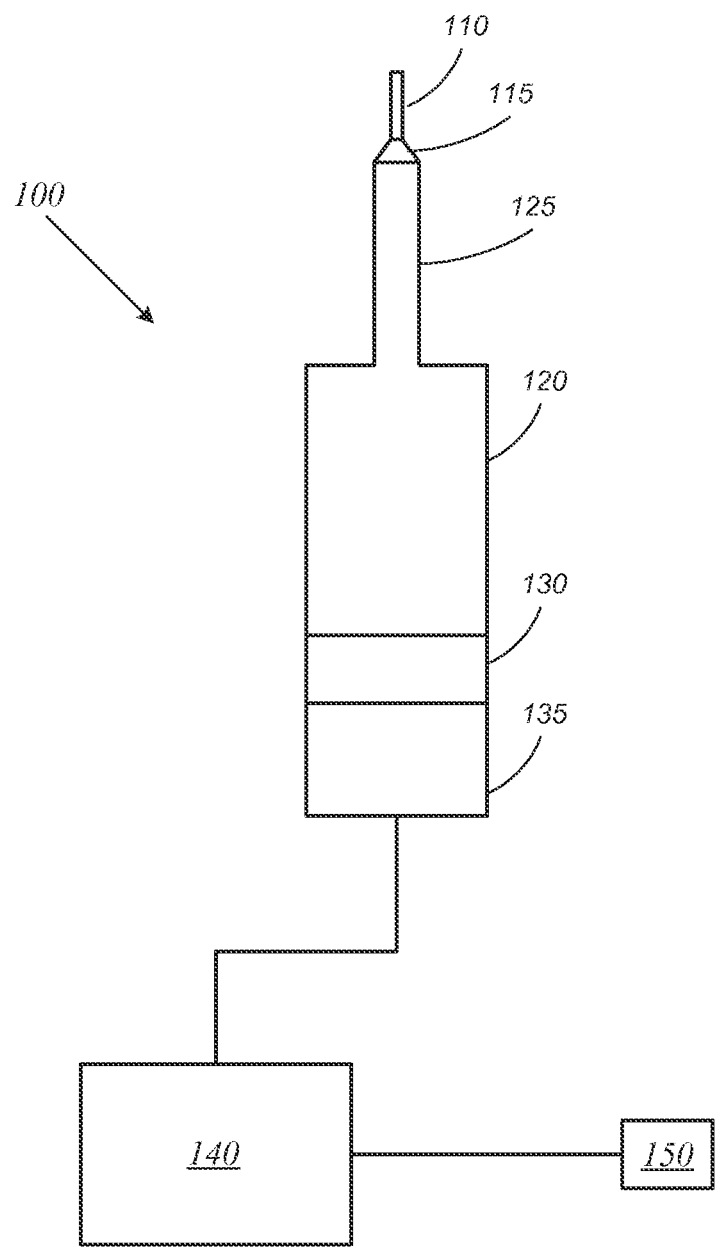
FIG. 1 is a block diagram of a surgical hand piece system.

FIG. 1 depicts an ultrasonic hand piece system. In FIG. 1, hand piece 100 is coupled to console 140. Console 140 is coupled to foot switch 150. Hand piece 100 has a cutting needle 110, a horn 120, a set of piezoelectric crystals 130, and a nut 135 that secures the piezoelectric crystals 130 to the horn 120. A needle interface 115 connects cutting needle 110 to a reduced diameter portion 125 of horn 120.

Needle 110 is typically a thin needle made of titanium or stainless steel that is designed to emulsify a lens when vibrated ultrasonically. Needle 110 is typically cylindrical in shape, has a small diameter of about 20-30 gauge, and has a length suitable for removal of a lens when inserted into the anterior chamber of the eye.

Horn 120 is typically made of a rigid material suitable for medical use (such as a titanium alloy). Horn 120 has a reduced diameter section 125 that is connected to a needle interface 115. Needle interface 115 typically has a threaded connection that accepts needle 110. In this manner needle 110 is screwed onto horn 120 at needle interface 115. This provides a rigid connection between needle 110 and horn 120 so that vibration can be transmitted from horn 120 to needle 110.

Piezoelectric crystals 130 supply ultrasonic vibrations that drive both the horn 120 and the attached cutting needle 110 during phacoemulsification. Piezoelectric crystals 130 are secured against horn 120 by nut 135. Piezoelectric crystals 130 are typically constructed from a plurality of crystal segments. When excited by a signal from console 140, piezoelectric crystals 130 resonate, producing vibration in horn 120.

Console 140 includes a signal generator that produces a signal to drive piezoelectric crystals 130. Console 140 has a suitable microprocessor, micro-controller, computer, or digital logic controller to control the signal generator. In operation, console 140 produces a signal that drives piezoelectric crystals 130. Piezoelectric crystals 130, when excited, cause horn 120 to vibrate. Needle 110, connected to horn 120, also vibrates. When needle 110 is inserted into the anterior chamber of the eye and vibrated, it acts to emulsify a cataractous lens.

Figure 2:
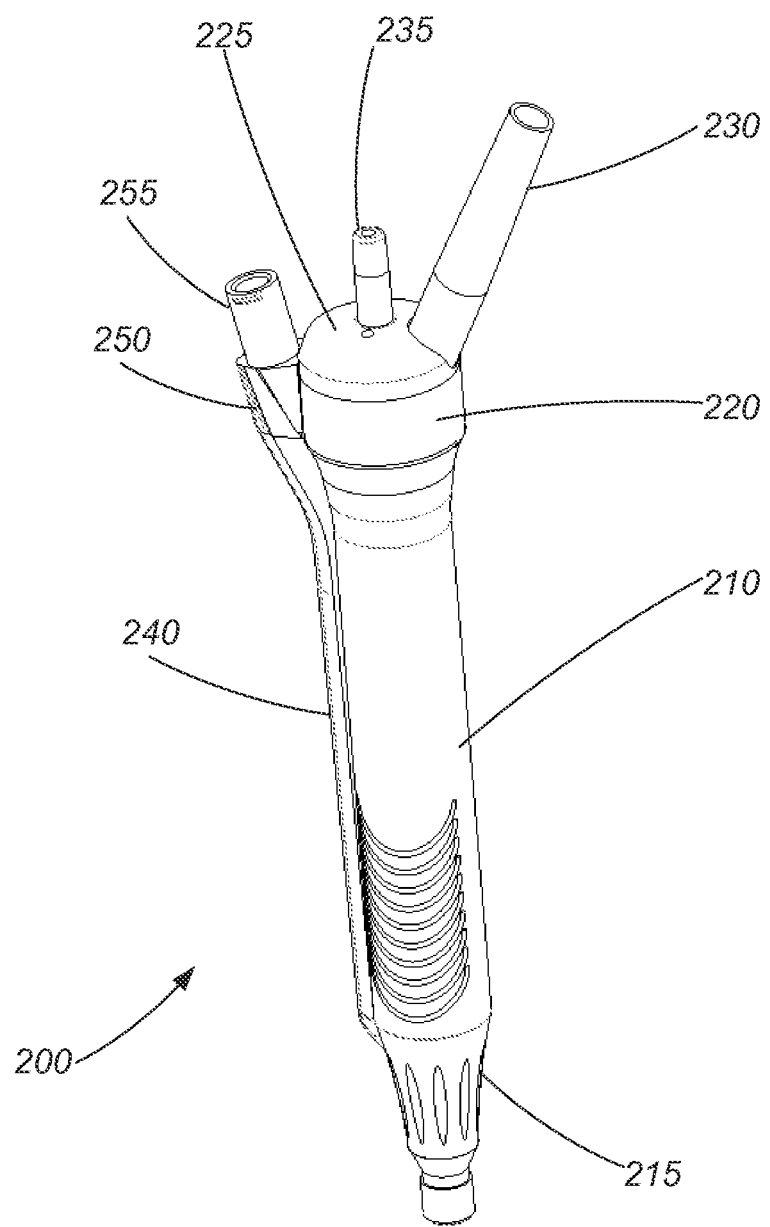
FIG. 2 is a perspective view of a surgical hand piece.

FIG. 2 is a perspective view of a surgical hand piece. In the example of FIG. 2, hand piece 200 has a shell 210 with proximal and distal ends. A nose cone 215 occupies the distal end of shell 210. A plug bolt weldment 220 is coupled to the proximal end of shell 210. An end cap 225 is coupled to the plug bolt weldment 220. Control cable connector 230 is coupled to end cap 225. An aspiration connector 235 protrudes through end cap 225. A channel 240 is coupled to shell 210. Channel 240 has distal and proximal ends. A sensor housing 250 is coupled to the proximal end of channel 240. The distal end of channel 240 is coupled to shell 210 at or near nose cone 215. An irrigation connector 255 is coupled to sensor housing 250.

Figure 3:
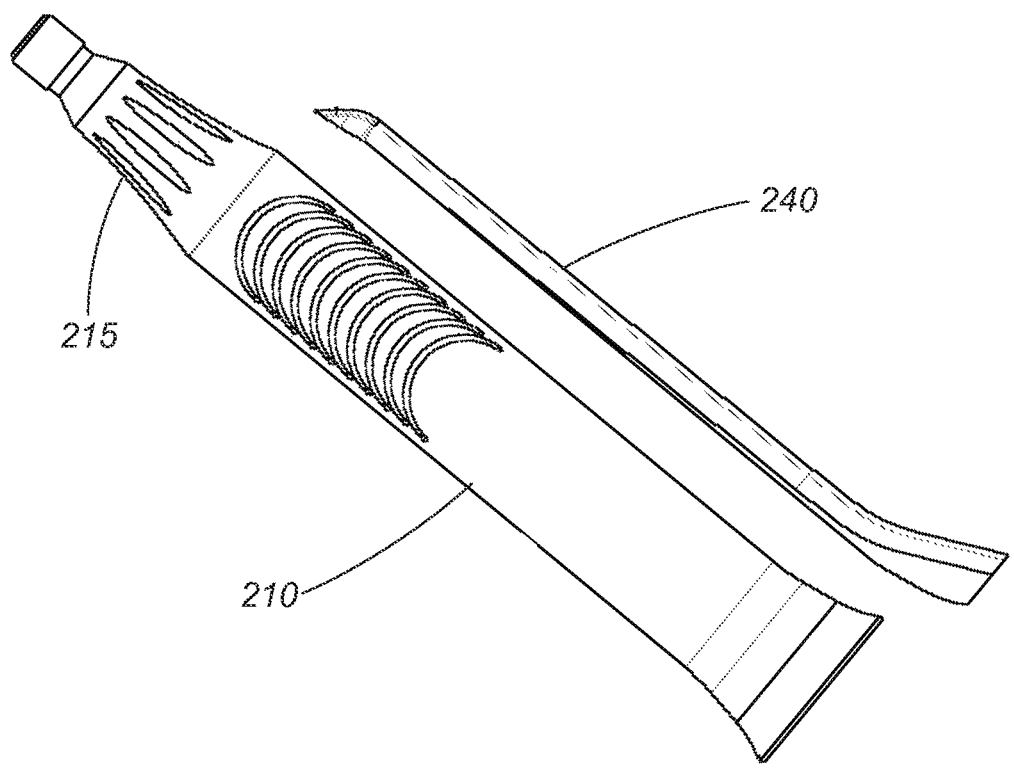
FIG. 3 is a side view of a portion of a surgical hand piece.

FIG. 3 is a side view of a portion of a surgical hand piece. In the example of FIG. 3, channel 240 is separated from shell 210. Shell 210 forms the outer portion of the hand piece and is held by a surgeon during surgery. Shell 210 is ergonomic and may include features to facilitate easy handling and manipulation of the hand piece. Shell 210 typically encloses other parts of the hand piece including the horn 120, reduced diameter section of the horn 125, piezoelectric crystals 130 and nut 135. Shell may be made of any durable material such as stainless steel. In such a case, channel 140 is typically welded to shell 210. Channel 140 forms part of an irrigation pathway that carries irrigation fluid to the eye during surgery. Channel 140 has an internal irrigation conduit that carries irrigation fluid. In use, irrigation fluid travels through channel 240 from its proximal end to its distal end. Irrigation fluid exits the distal end of channel 240 through an opening. A corresponding opening in shell 210 is coextensive with the opening on distal end of channel 240. In this manner, irrigation fluid travels through channel 240 and into shell 210. From there, the irrigation fluid travels through a passage in shell 210 (typically between an interior surface of shell 210 and the distal end of horn 120 or reduced diameter section 125 of horn 120). Irrigation fluid then exits the distal end of shell 210 and is carried to the eye via a sleeve that surrounds needle 110.

Figure 4:
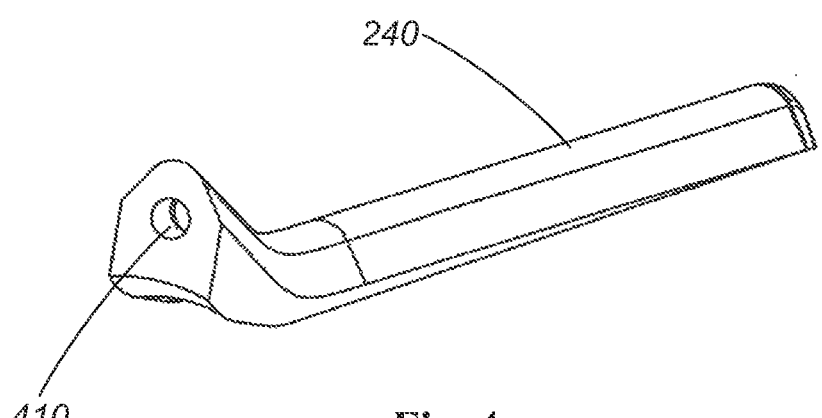
FIG. 4 is a perspective view of a channel portion of a surgical hand piece.

FIG. 4 is a perspective view of a channel portion of a surgical hand piece. In FIG. 4, an irrigation conduit 410 is shown on proximal end of channel 240. Irrigation conduit 410 extends through the length of channel 240 and terminates at an opening on or near the distal end of channel 240.

Figure 5:
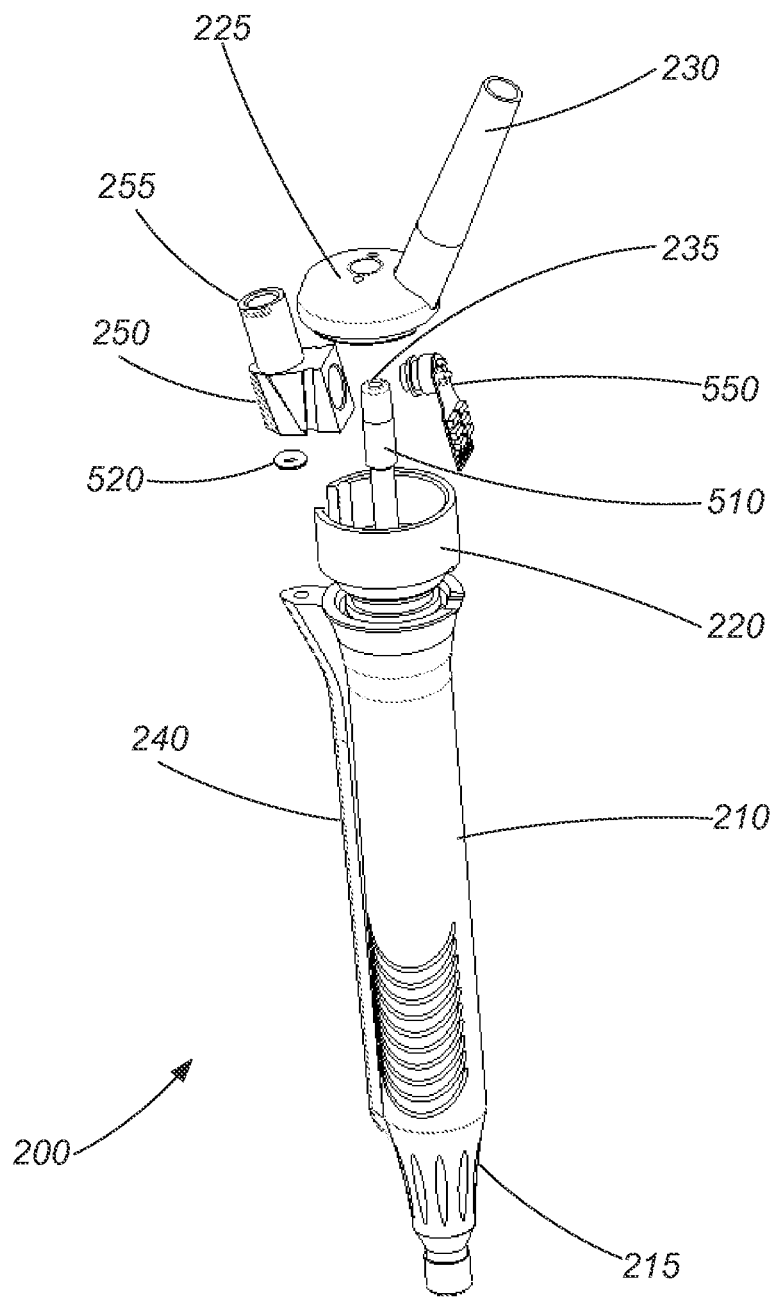
FIG. 5 is an exploded view of a surgical hand piece.

FIG. 5 is an exploded view of a surgical hand piece. In the example of FIG. 5, hand piece 200 has a shell 210 with proximal and distal ends. A nose cone 215 occupies the distal end of shell 210. A plug bolt weldment 220 is coupled to the proximal end of shell 210. Plug bolt weldment 220 has a hollow interior. An aspiration conduit 510 extends from plug bolt weldment 220. An end cap 225 is coupled to the plug bolt weldment 220. Control cable connector 230 is coupled to end cap 225. An aspiration connector 235 protrudes through end cap 225. A channel 240 is coupled to shell 210. Channel 240 has distal and proximal ends. Irrigation conduit 410 extends from the proximal end of channel 240 to its distal end. A sensor housing 250 is coupled to the proximal end of channel 240. A seal 520 is located between the proximal end of channel 240 and the sensor housing 250. The distal end of channel 240 is coupled to shell 210 at or near nose cone 215. An irrigation connector 255 is coupled to sensor housing 250. A sensor assembly 550 fits into sensor housing 250.

In FIG. 5, sensor housing 250 provides a secure location for sensor assembly 550. Sensor housing 250 is securely coupled to plug bolt weldment 220. Sensor assembly 550 is located in sensor housing 550. When assembled, end cap 225 is secured to plug bolt weldment 220. Plug bolt weldment 220 is secured to proximal end of shell 210. Seal 520 provides a liquid tight seal between sensor housing 250 and channel 240. Plug bolt weldment 220 has a hollow interior that provides a space for wire connections to sensor assembly 550. Portions of the sensor assembly 550 may be located in the hollow interior of plug bolt weldment 220.

Sensor assembly 550 measures the pressure of the irrigation fluid traveling through sensor housing 250. Irrigation fluid travels from an irrigation source (typically a bottle or a bag) through flexible tubing to hand piece 200. One end of the flexible tubing is coupled to the irrigation source, and the other end of the flexible tubing is coupled to hand piece 200 at irrigation connector 255. In this case, irrigation connector 255 is a luer lock connector, but numerous other types of connectors may be employed. Irrigation fluid enters hand piece 200 at irrigation connector 255 and travels through a passage in sensor housing 250. The irrigation fluid then travels through irrigation conduit 410 in channel 240 and into shell 210 at or near nose cone 215. The irrigation fluid continues through a passage in nose cone 215 and exits shell 210 at the end of nose cone 215. The irrigation fluid is then carried to the eye through a sleeve (not shown) that is coupled to the end of nose cone 215. In this manner, a continuous path is provided for the introduction of irrigation fluid into the eye during surgery. This continuous fluid path passes through the length of hand piece 200. Because sensor assembly 550 is located along the irrigation fluid path at a point that is very close to the eye, sensor assembly 550 more accurately measures the pressure in the eye. Typically, hand piece 210 is about four to six inches long. Accordingly, pressure sensor assembly 550 measures the pressure of fluid about four to six inches from the eye.

In currently available surgical systems, pressure sensors are located a much greater distance from the eye. For example, in typical cataract systems, an irrigation pressure sensor would be located on a surgical console. A long length of flexible tubing connects the console to the hand piece and carries irrigation fluid. Moreover, this flexible tubing is typically made of a polymer with a certain degree of compliance. In this manner, the pressure sensor is located at one end of the flexible tubing. The other end of the flexible tubing is connected to the hand piece. Because of the length of flexible tubing located between the pressure sensor and the eye, the pressure sensor does not accurately measure the pressure in the eye. As can be appreciated, a more accurate reading of the pressure in the eye results in better control of fluidics during surgery. Locating sensor assembly 550 in hand piece 200 provides for a more accurate reading of eye pressure.

Turing again to the example of FIG. 5, plug bolt weldment provides space to house a portion of sensor housing 250 and sensor assembly 550. As will be better appreciated with reference to FIG. 8, wiring can be located in plug bolt weldment 220 to provide a pressure reading from sensor assembly 550 to a cable at control cable connector 230.

Figure 6:
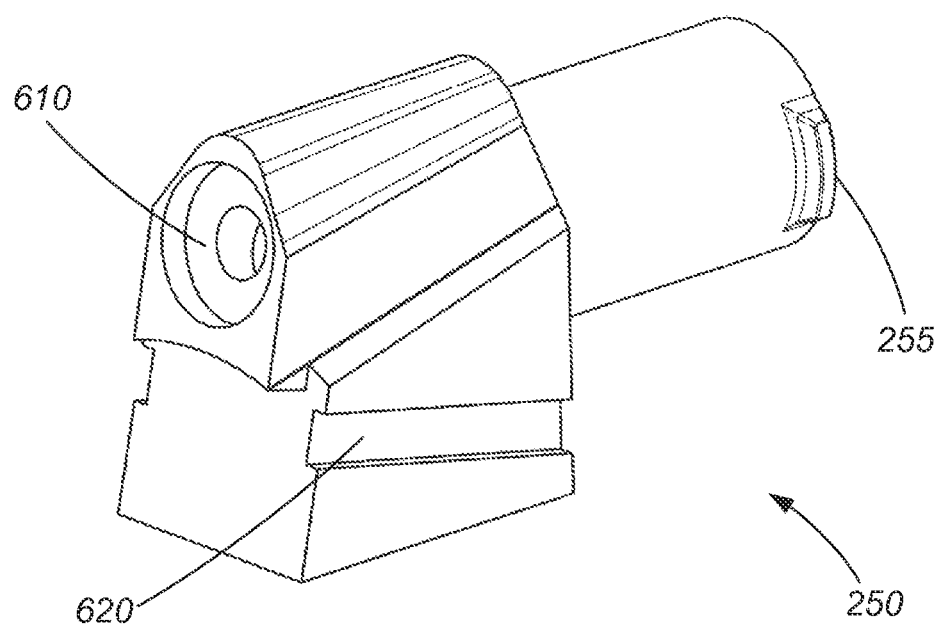
FIG. 6 is a perspective view of a sensor housing for a surgical hand piece.

FIG. 6 is a perspective view of a sensor housing for a surgical hand piece. In the example of FIG. 6, sensor housing 250 includes an irrigation connector 255, a seal interface 610, and a groove 620. Irrigation connector 255 receives one end of a length of flexible tubing that carries irrigation fluid. Seal interface has a recess that accepts seal 520. In this case, seal 520, in its simplest form, is a washer that provides a fluid tight seal between sensor housing 250 and channel 240. Sensor housing 250 is coupled to plug bolt weldment 220 at groove 620. In this example, sensor housing 250 slides into a notch in plug bolt weldment 220. The groove 620 engages the slot in plug bolt weldment 220.

Figure 7:
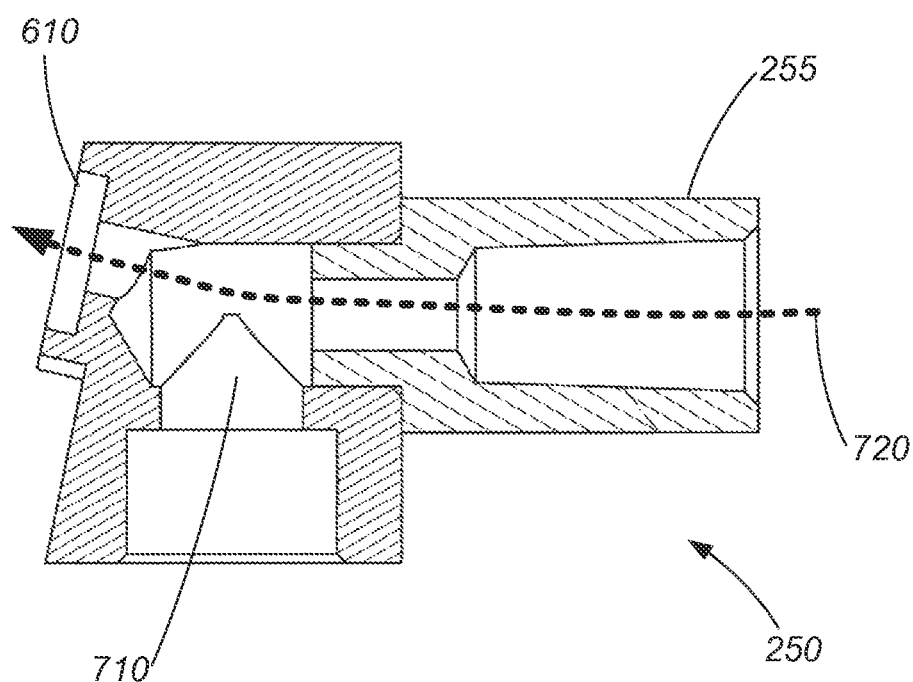
FIG. 7 is a cross section view of a sensor housing for a surgical hand piece.

FIG. 7 is a cross section view of a sensor housing for a surgical hand piece. In the example of FIG. 7, sensor housing 250 includes an irrigation connector 255, a seal interface 610, and a cavity 710 for receiving pressure sensor assembly 550 (and more particularly, pressure sensor 810). An irrigation fluid path 720 is shown by the dashed line in FIG. 7. The irrigation fluid path 720 extends through sensor housing 250 from the end with the irrigation connector 255 to the end with the seal interface. In this manner, irrigation fluid path 720 provides a continuous path through which irrigation fluid can pass through sensor housing 250. The cavity 710 is in fluid communication with irrigation fluid path 720. In this manner, a pressure sensor located in cavity 710 can measure the pressure of fluid in irrigation fluid path 720.

Figure 8:
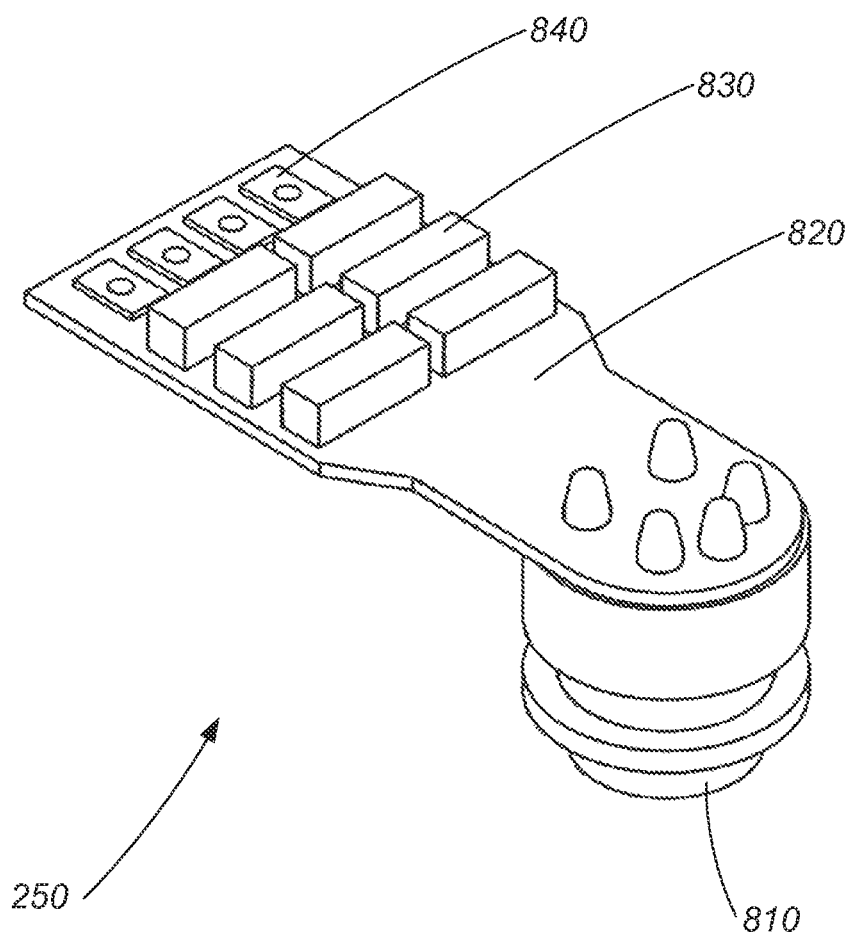
FIG. 8 is a perspective view of a sensor assembly for a surgical hand piece.

FIG. 8 is a perspective view of a sensor assembly for a surgical hand piece. In the example of FIG. 8, sensor assembly 550 includes a pressure sensor 810, a flex circuit 820, circuitry 830, and wire terminations 840. Pressure sensor 810, circuitry 830, and wire terminations 840 are all mounted on flex circuit 820. Pressure sensor 810 is sized and shaped to fit into cavity 710 of sensor housing 250. In this manner, the cavity 710 is sized and shaped to accommodate pressure sensor 810. Pressure sensor 810 fits within cavity 710 and provides a fluid tight seal. Pressure sensor 810 may be enclosed in a polymer to provide this fluid tight seal. When assembled, the flex circuit 820 is located in plug bolt weldment 220. Wires coupled to wire terminations 840 are also located in plug bolt weldment 220 and can extend to control cable connector 230.

From the above, it may be appreciated that the present invention provides an improved surgical hand piece for cataract surgery. The present invention provides a hand piece with an integrated pressure sensor for improved pressure measurement during surgery. The present invention is illustrated herein by example, and various modifications may be made by a person of ordinary skill in the art. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A surgical hand piece comprising:
a shell having proximal and distal ends;
a channel having proximal and distal ends, the channel coupled to the shell such that the proximal end of the channel is located at the proximal end of the shell and the distal end of the channel is located near the distal end of the shell, the channel having an irrigation conduit;

a sensor housing comprising an irrigation path extending through the sensor housing, the sensor housing comprising a seal interface on one end of the sensor housing, the seal interface end of the sensor housing coupled to the proximal end of the channel such that the irrigation conduit of the channel is fluidly coupled to the irrigation path of the sensor housing.

2. The surgical hand piece of claim 1 wherein the sensor housing further comprises a cavity for receiving a pressure sensor.

3. The surgical hand piece of claim 2 further comprising:
a pressure sensor assembly comprising a pressure sensor, the pressure sensor located in the cavity.

4. The surgical hand piece of claim 3 wherein the pressure sensor fluidly seals the cavity.

5. The surgical hand piece of claim 3 wherein the pressure sensor measures fluid pressure in the irrigation path of the sensor housing.

6. The surgical hand piece of claim 3 wherein the pressure sensor assembly further comprises:
a flex circuit;
circuitry coupled to the flex circuit; and
wire terminations coupled to the flex circuit;
wherein the pressure sensor is coupled to the flex circuit.

7. The surgical hand piece of claim 1 further comprising:
a plug bolt weldment coupled to the sensor housing and the proximal end of the shell, the plug bolt weldment having a hollow interior.

8. The surgical hand piece of claim 1 further comprising:
a pressure sensor assembly at least partially located in the hollow interior of the plug bolt weldment.

9. The surgical hand piece of claim 1 wherein the sensor housing further comprises:
an irrigation connector.

10. The surgical hand piece of claim 1 further comprising:
a seal located at the seal interface of the sensor housing.

11. A surgical hand piece comprising:
a shell having proximal and distal ends;
a channel having proximal and distal ends, the channel coupled to the shell such that the proximal end of the channel is located at the proximal end of the shell and the distal end of the channel is located near the distal end of the shell, the channel having an irrigation conduit;

a sensor housing comprising an irrigation path extending through the sensor housing, the sensor housing comprising a seal interface on one end of the sensor housing, the seal interface end of the sensor housing coupled to the proximal end of the channel such that the irrigation conduit of the channel is fluidly coupled to the irrigation path of the sensor housing, the sensor housing further comprising a cavity;

a pressure sensor assembly comprising a flex circuit, a pressure sensor coupled to the flex circuit, the pressure sensor located in the cavity of the sensor housing, the pressure sensor measuring fluid pressure in the irrigation path.

12. The surgical hand piece of claim 11 wherein the pressure sensor fluidly seals the cavity.

13. The surgical hand piece of claim 11 wherein the pressure sensor assembly further comprises:
circuitry coupled to the flex circuit; and
wire terminations coupled to the flex circuit.

14. The surgical hand piece of claim 11 further comprising:
a plug bolt weldment coupled to the sensor housing and the proximal end of the shell, the plug bolt weldment having a hollow interior.

15. The surgical hand piece of claim 14 wherein the pressure sensor assembly is at least partially located in the hollow interior of the plug bolt weldment.

16. The surgical hand piece of claim 11 wherein the sensor housing further comprises:
an irrigation connector.

17. The surgical hand piece of claim 11 further comprising:
a seal located at the seal interface of the sensor housing.

18. The surgical hand piece of claim 14 further comprising:
an end cap coupled to the plug bolt weldment and sealing the hollow interior of the plug bolt weldment.

19. The surgical hand piece of claim 11 further comprising:
a nose cone located at the distal end of the shell.

20. The surgical hand piece of claim 19 wherein the distal end of the channel terminates at the nose cone.

* * * * *